US005925229A

United States Patent [19]
Krauss et al.

[11] Patent Number: 5,925,229
[45] Date of Patent: *Jul. 20, 1999

[54] LOW DENSITY LIPOPROTEIN FRACTION ASSAY FOR CARDIAC DISEASE RISK

[75] Inventors: Ronald M. Krauss; Patricia J. Blanche, both of Berkeley; Joseph Orr, San Pablo, all of Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/642,296

[22] Filed: May 3, 1996

[51] Int. Cl.$^6$ .......................... G01N 27/26; G01N 27/447
[52] U.S. Cl. ............................................. 204/606; 204/469
[58] Field of Search ..................................... 204/456, 469, 204/466, 467, 470, 606, 616, 618

[56] References Cited

U.S. PATENT DOCUMENTS

| 5,387,325 | 2/1995 | Opplt ....................................... 204/616 |
| 5,589,104 | 12/1996 | Bambeck ............................. 204/469 X |

FOREIGN PATENT DOCUMENTS

| 9325897 | 12/1993 | European Pat. Off. ................ 204/469 |
| 1-173858 | 7/1989 | Japan ..................................... 204/606 |

OTHER PUBLICATIONS

David L. Rainwater et al "Production of polyacrylamide gradient gels for the electrophoretic resolution of lipoproteins " Journal of Lipid Reasearch, vol. 33, pp. 1876–1881, No month available, 1992.

Rainwater, Audres, Ford, Lowe, Blanche & Krauss "Production of Polyacryamide Gradient Gels for electrophoretic resolution of Lipoproteins"*J. Lipid Research* vol. 33, p. 1876, No month available,1992.

Singh, Rainwater et al "Effect of Diabetes on Lipoprotein Size" *Arteriosclerosis, Thrombosis, and Vascular Biology* vol. 15, p. 1805, No month available, 1995.

Krauss & Blanche "Detection and quantitation of LDL subfractions" *Current Opinion in Lipidology* vol. 3, p. 377, No month available, 1992.

Krauss "Low Density Lipoprotein Subclasses and Risk of Coronary Artery Disease" *COL*, vol. 2, p. 248, No month available, 1991.

Nichols, Krauss & Musliner, "Nondenaturing Polyacrylamide Gradient Electrophoresis" *Methods in Enzymology* vol. 128, p. 417, No month available, 1986.

Krauss & Burke "Identification of Multiple subclasses of Plasma Low Density Lipoproteins in Normal Humans" *J. of Lipid Research*, vol. 23, p. 97, No month available, 1982.

Williams, Vranizan & Krauss "Correlations of Plasma Lipoproteins with LDL Subfractions by Particel Size in Men and Women" No month available *J of Lipid Research* vol. 33, p. 765, 1992.

*Primary Examiner*—William H. Beisner
*Assistant Examiner*—John S. Starsiak, Jr.
*Attorney, Agent, or Firm*—Paul R. Martin; Henry Sartorio; David J. Aston

[57] ABSTRACT

A variable rate density gradient electrophoric gel is described which separate LDL subfractions with the precision of ultracentrifugation techniques. Also, an innovative bottom inlet mixing chamber particularly useful for producing these gels is described.

12 Claims, 5 Drawing Sheets

| GRADIENT CURVE - F*/8 2-14% POLYACRYLAMIDE GELS | | | | |
|---|---|---|---|---|
| SOLVENT 1 = 2% ACRYLAMIDE | | | | |
| SOLVENT 2 = 14% ACRYLAMIDE | | | | |
| SEGMENT NUMBER | FLOW RATE mL/MIN. | % SOLVENT 2 START | END | DURATION MIN. |
| 1 | 7 | 0 | 14.1 | 1.5 |
| 2 | 7 | 14.1 | 64.5 | 13.5 |
| 3 | 7 | 64.5 | 100 | 5.3 |
| 4 | 0 | 0 | 0 | 0.5 |
| 5 | 4 | 100 | 100 | 5.0 |

LOW DENSITY LIPOPROTEIN FRACTION ASSAY FOR CARDIAC DISEASE RISK

This invention was made with U.S. Government support under Contract No. DE-AC03-76SF00098 between the U.S. Department of Energy and the University of California for the operation of Lawrence Berkeley Laboratory and under a grant by the National Institute of Health. The U.S. Government has certain rights in this invention.

BACKGROUND OF THE INVENTION

This invention relates generally to medical diagnostics for quantitative analysis of low density lipoprotein fractions and assignment of cardiac disease risk.

Lipoproteins

Lipoproteins are complex molecules found in the blood. One of the biological actions of lipoproteins in the circulatory system is to transport cholesterol for cellular use. Lipoproteins are subdivided into classes and subclasses on the basis of density, which is determined by equilibrium density ultracentrifugation and analytic ultracentrifugation, or size, which is determined by gel electrophoresis. The classes which have been assigned to various lipoprotein fractions are: very low density lipoprotein (VLDL), intermediate density lipoprotein (IDL), low density lipoprotein (LDL) and high density lipoprotein (HDL).

Ultracentrifugally isolated lipoproteins, analyzed for flotation properties by analytic ultracentrifugation in two different salt density backgrounds, allows for the determination of hydrated LDL particle density. (Lindgren et al, Wiley, 1992 p. 181–274.) A comparison of LDL particle densities from 642 subjects shows a distinct bimodality separating groups with particles greater than and less than 1.032 gm/ml. In the group with LDL, d.$\geq$1.032 gm/ml, there is a higher correlation of coronary artery disease risk factors including elevated plasma triglycerides, increased body mass index and history of familial coronary disease.

The LDL class can be further divided into seven subclasses based on density or particle diameter using a preparative separation technique, equilibrium density gradient ultracentrifugation (EDGU). Elevated levels of specific LDL subclasses, LDL-IIIa, IIIb and IV a, and their related cholesterols, is the clinical finding which correlates most closely with increased risk for coronary artery disease, including atherosclerosis.

The determination of total serum cholesterol levels is used routinely as a diagnostic test. Because it is expensive and time-consuming, determination of the more predictive lipoprotein class and subclass distribution is typically ordered by physicians only for a very limited number of patients.

LDL Quantitation

Currently, the most widely used method for quantitating LDL cholesterol is the indirect Friedewald method (Friedewald, et al., Clin. Chem. Vol. 18, pp.499–502, 1972). The Friedewald assay method requires three steps: 1) determination of plasma triglyceride (TG) and total cholesterol (TC); 2) precipitation of VLDL and LDL, and 3) quantitation of HDL cholesterol (HDL-C). Using an estimate for VLDL-C as one-fifth of plasma triglycerides (TG/5), the LDL cholesterol concentration (LDL-C) is calculated by the formula: LDL-C=TC−(HDL-C+VLDL-C).

While generally useful, the Friedewald method is limited in its accuracy in specific cases. Errors can occur in any of the three steps, in part because this method requires that different procedures be used in each step. The Friedewald method presumes that VLDL-C concentration is one-fifth that of plasma triglycerides. When the VLDL of some patients deviates from this ratio, further inaccuracies occur. For patients with TG over 400 mg/dL, the Friedewald method cannot be used.

Otvos teaches a procedure for determining concentrations of lipoprotein subclasses which allows greater accuracy than Friedewald (U.S. Pat. No. 5,343,389, issued Aug. 30, 1994). Otvos initially obtains the NMR chemical shift spectrum of a blood plasma or serum sample. The observed spectrum of the whole plasma sample is then matched with weighted sums of NMR spectra of lipoprotein subclasses, which are stored in a computer software program. The weighting factors which give the best fit between the sample spectrum and the calculated spectrum are then used to estimate the concentrations of constituent lipoprotein subclasses in the blood sample. This procedure has the additional advantage of being rapid.

Another lipoprotein subfraction determination method that is used clinically is the Vertical Auto Profile (VAP), (Kulkarni, et al., J. Lip. Res. Vol. 35, pp.159–168, 1994). VAP uses a flow analyzer for the enzymatic analysis of cholesterol in lipoprotein classes separated by a short spin single vertical ultracentrifuge, and subsequent spectrophotometry and software analysis of the resulting data. While a useful advancement, this technique does not resolve the LDL into all seven subspecies isolated by ultracentrifugation.

Gel Separation

The subject inventors previously have developed a procedure using gradient gel electrophoresis for separation of LDL subclasses. The LDL subfractions separated by the gradient gel electrophoresis are comparable to those obtained by ultracentrifuge. This method makes a finer resolution of LDL subclasses available to research laboratories. It would be useful if gradient gel electrophoresis separation could be shortened and simplified so that it could be used in clinical laboratories as part of a routine screening of blood samples, to assign a risk factor for coronary artery disease.

A high resolution assay for measuring LDL cholesterol that would be accurate, direct, and complete, quantitating all major subclasses of LDL would be an important innovation in this technology. If inexpensive and convenient, it could be employed in a clinical laboratory setting. Ideally, clinicians could assign a patient risk factor for CAD, and correlate concentrations of LDL subclasses with the more commonly used LDL-cholesterol concentrations for conventional use.

SUMMARY OF THE INVENTION

The inventive assay for the first time allows the practical, clinically useful prediction of a patient's risk of coronary artery disease, including atherosclerosis. The inventive electrophoretic gel provides variable rate of density which allows separation of LDL subfractions and the prediction of patients' risk of heart disease. A mixing chamber particularly suited to the production of these innovative gels is also provided.

It is an object of the present invention to accurately quantitate up to seven LDL cholesterol subclasses (differentiated by particle diameter) in a plasma sample, and to assign a corresponding patient risk factor for CAD.

It is a further object of the present invention to provide a rapid and inexpensive assay for this quantitation, for use in a clinical laboratory.

It is an additional object of the present invention to provide a mixing chamber with innovative features well-suited to the production of the inventive gels.

According to the present invention, a plasma sample from a patient is separated into discrete constituent lipoprotein subspecies according to particle diameter by nondenaturing gradient gel electrophoresis using the inventive variable rate density gradient gels. Calibration markers are concurrently separated on the gel, to allow assignment of particle diameter values to discrete LDL subspecies. Because there are only small variations in sphericity among the LDL, the migration distance of each particle is inversely related to particle diameter.

The concentration of each discrete LDL subspecies, defined by particle diameter relative to the calibration marker, is determined by integration of the area of its peak on the densitometry scan. A corresponding cholesterol concentration and patient CAD risk is then assigned based on comparison to accumulated patient data. This can be accomplished using computer software.

The inventive assignment of patient CAD risk is based on levels of LDL subfractions IIIa, IIIb, and IVa. From population studies, it has been determined that high levels of this combination of subfractions is a relatively discrete and stable marker for an atherogenic lipoprotein phenotype.

Using the present invention, it is possible to make highly sophisticated determinations of LDL subfractions in a clinical laboratory. An important advantage of the present invention is that it includes various embodiments that allow large number of plasma samples to be routinely analyzed for LDL subspecies by electrophoretic equipment and computer software available to a clinical laboratory. These simplified, clinical tests provide the same results as those obtained by the expensive, time-consuming and complicated process of analytical ultracentrifugation The subject invention allows patients to be screened during routine blood analysis for risk of coronary artery disease.

DETAILED DESCRIPTION OF THE INVENTION

Figures 2, 5:
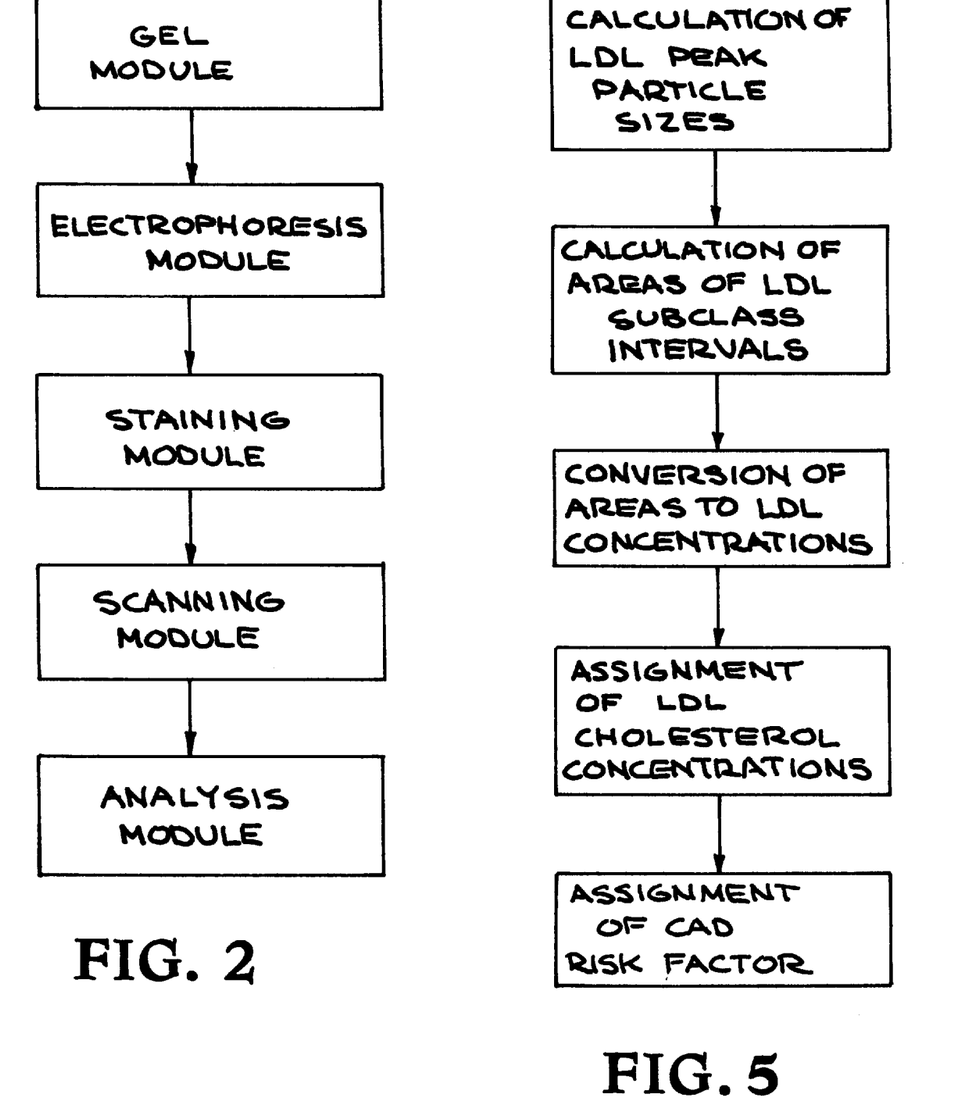
FIG. 2 is a depiction of the five modules contained within the inventive apparatus.
FIG. 5 shows the five analytical steps performed by software analysis of the densitometric scans.

The present invention is a variable rate density gradient electrophonetic gel, which is used in a clinical apparatus to determine with high resolution the concentrations of LDL subspecies within a plasma sample from a patient. Analysis by appropriate software provides assignment of corresponding cholesterol concentrations and risk for coronary artery disease. As shown in FIG. 2, the apparatus comprises a gel module, an electrophoresis module, a staining module, a scanning module, and an analysis module.

LDL Subspecies Separation and Analysis

I. Gel Preparation

Figure 3:
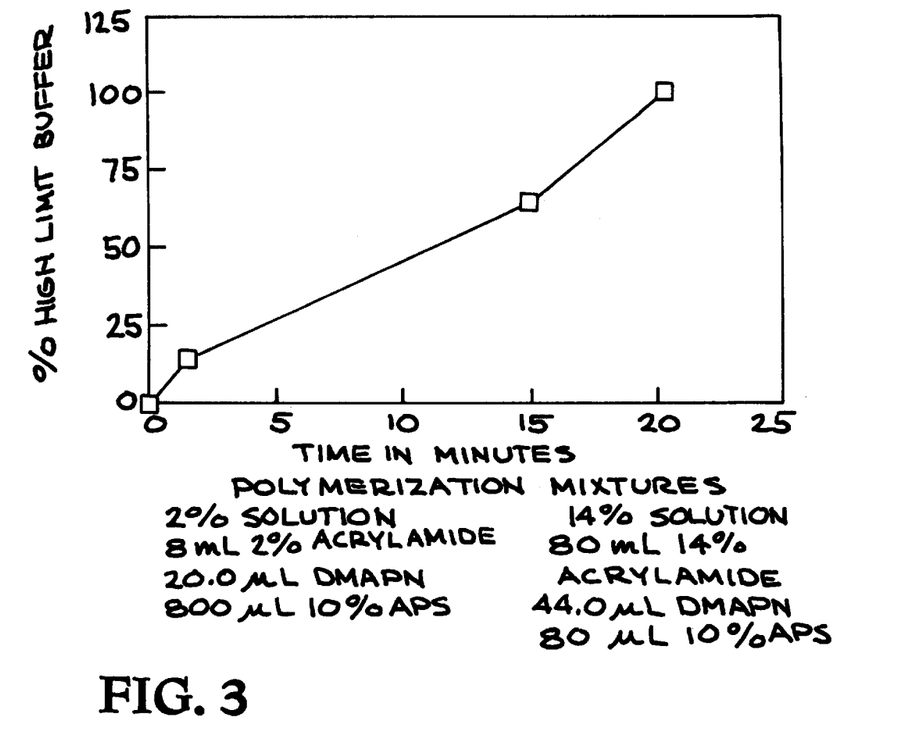
FIG. 3 correlates the gel polymerization time with the percentage of high limit buffer.
Figure 4:
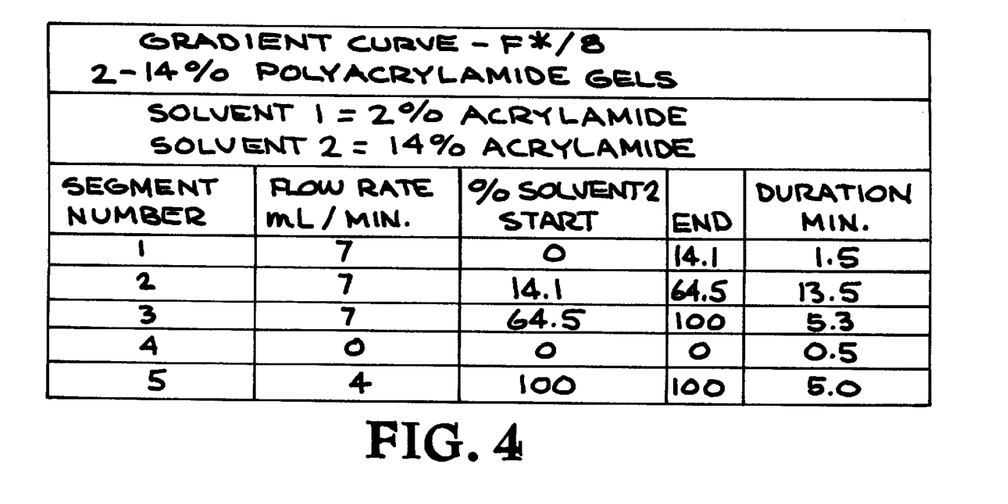
FIG. 4 shows the flow rates and durations through each of the identified segments.

According to the present invention, a plasma sample is separated into its constituent LDL subspecies by nondenaturing gradient gel electrophoresis. Referring to FIG. 3 and FIG. 4, the most preferred embodiment of the gel module 3 is shown. A polyacrylamide gradient gel is cast in three intervals between two glass plates in a controlled manner to allow reproducible separation of seven subspecies of LDL, differentiated by particle size.

Gel Cassettes

Gel cassettes are assembled (Pharmacia technical bulletin, *Polyacrylamide Gel Electrophoresis,* revised edition, Uppsala, Sweden), with two seals of waterproof tape. In one embodiment of the invention, prefabricated plastic cassettes are used to simplify the assembly of cassettes with tight seals. Tight seals on the cassettes at this stage eliminates the formation or bubbles between the plates and the gel during electrophoresis. In an alternate embodiment, the glass plates of the cassette are pretreated with a film of bonding material to aid in the bonding of the gel to the glass.

Gel Materials

The gradient gel is prepared from two stock solutions: 1) a high-limit solution of acrylamide and bis-acrylamide, and 2) a low-limit solution of acrylamide and bis-acrylamide. As described by FIG. 3, in the most preferred embodiment of the invention the amounts of catalysts added are: 1% of 10% ammonium persulfate and 0.022% DMAPN in the low-limit solution, and 0.1% of 10% ammonium persulfate and 0.05% DMAPN in the high-limit solution.

In the most preferred embodiment of the invention, the gel is cast in three controlled steps, as described in FIGS. 3 and 4, with an initial gradient slope of 1.9 (% increase high limit buffer/% gel length), followed by a second gradient slope of 0.76, and a third slope of 1.36. In one specific embodiment, the second gradient slope is 0.76 and the third slope is 1.4.

In one embodiment of the invention, a 2%–9% polyacrylamide gradient gel is cast. This embodiment requires the use of suitable standards, such as frozen low density lipoprotein standards, to accommodate the smaller range of particle sizes that can be resolved on this gel. Only 2 cm length of the 2% to 14% gradient gel yields useful information about LDL subspecies. Shortening the gradient gel reduces both the cost of materials and the time required to process samples.

Greater differentiation can be achieved using a 1% to 9% polyacrylamide gradient gel. The 1% low limit to the gradient gel allows resolution of larger LDL subfractions which cannot be differentiated in a 2% gel. Using standard casting procedures, a 1% gel is too fragile for electrophoresis purposes. The 1%–9% polyacrylamide of the present invention is structurally strengthened by mixing the gel with agaros to avoid that limitation. Alternatively, the 1%–9% polyacrylamide gel can be strengthened by pouring a layer of agars above the polyacrylamide layer.

Gel Casting

Figure 1:
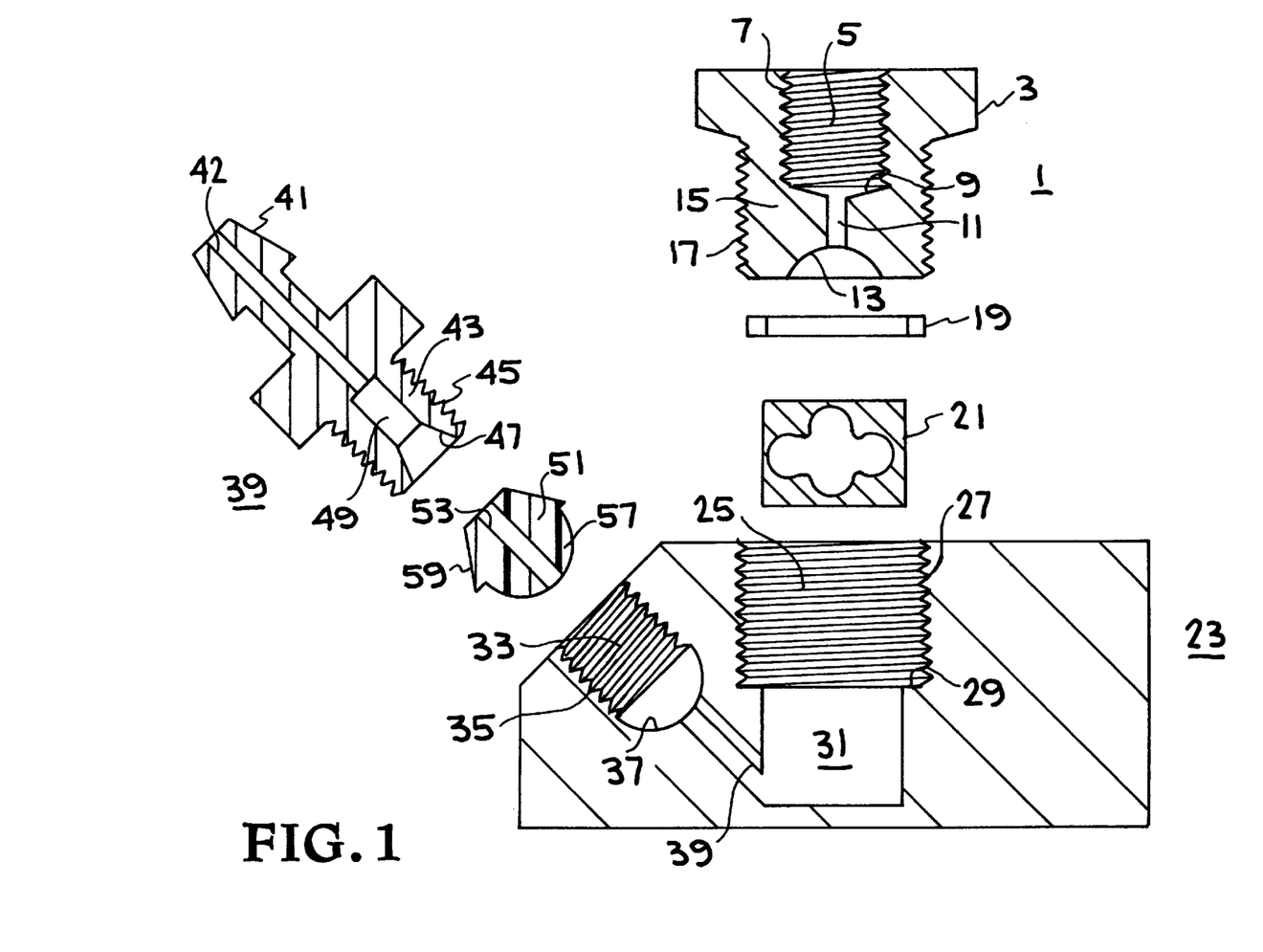
FIG. 1 is a drawing of the inventive gradient gel acrylamide mixing chamber.

A dual-pump gradient controller is used to cast the gradients. The solutions from the two pumps are mixed in an external mixing chamber before entering the casting stand into standard glass cassettes measuring 8 cm by 8 cm. As shown in FIG. 1, a preferred embodiment of the invention uses a custom-designed mixing chamber which allows the self-purging of air bubbles in the system.

The production of uniform and reproducible gradient gels is accomplished by means of an Apple II computer and ISCO Inc. software communicating through an electronic "Cheminterface" to two peristaltic pumps, Pump 1 and Pump 2 which together maintain a constant total rate of pumping. At the onset of the gradient program Pump 1 delivers at the total flow rate with no contribution from Pump 2. With each successive moment throughout the gradient run, Pump 1 delivers a successively lower output as Pump 2 simultaneously provides a successively greater output until Pump 2 alone delivers the full output at the end of the run.

A silastic tube runs from a supply of low percentage acrylamide solution to Pump 1, through the peristaltic pump mechanism and on to a "T" junction where it meets the corresponding tube from Pump 2 carrying its portion of high percentage acrylamide solution from a separate supply. The crude acrylamide mixture is carried through the "T" outlet to the inlet port of the mixing chamber where a thorough mixing of the high and low proportions of acrylamide is effected.

The mixed acrylamide solution exits the mixing chamber and continues through a plastic tube to the bottom of a casting chamber. The casting chamber holds up to eight gel cassettes vertically positioned within it so as to receive the acrylamide mixture from the bottom. A 20% ethanol solution within the casting chamber serves as an overlayer as progressively higher densities of acrylamide solution enter the casting chamber and are pushed upward into the cassettes. By the end of the gradient run, the 2% acrylamide layer rests within 8 mm of the top of the gel cassette and a linear gradient of increasing densities of acrylamide progresses toward the bottom of the gel cassettes where the final acrylamide concentration is 14%.

A pear-shaped flask with a tapered bottom is preferred as an acrylamide supply vessel for each acrylamide solution. This shape helps to keep the suction tubes submerged in acrylamide solution. This submerging reduces the chance that air may be introduced into the tubing conveying acrylamide solution to the gels. It also minimizes the volume of acrylamide solution needed to make a gel casting, and enhances mixing of acrylamide solution and catalysts by swirling instead of shaking, to prevent excess oxygen from disolving in the degassed solution.

Custom made flask holders were fashioned from a section of Lucite tube with a bottom piece of lucite glued within the inside diameter of the tube. A centrally placed hole in the bottom plate receives the pointed bottom of the pear shaped flask and holds the flask upright in the lucite tube section. These flask holders also keep the flasks upright in the vacuum chamber while the acrylamide solutions are being degassed.

Acrylamide solutions are degassed in a polycarbonate vacuum chamber 8" in diameter and 12" in height. The vacuum is supplied by a motor driven floor pump to produce a working vacuum of ca. 28 in. conveyed to the vacuum chamber through a length of vacuum hose. A large stir plate beneath the vacuum chamber drives a small stir bar in each solution flask to adequately circulate the acrylamide solutions and promote the removal of oxygen from the acrylamide solutions prior to polymerization. Excess oxygen in solution is known to hinder the acrylamide polymerization reaction.

The casting chamber with tubing connected is placed in a non-circulating water bath, set to the ideal acrylamide gel polymerization temperature of 25° C. Enough water is added to the bath to surround the casting chamber, providing a heat sink for the exothermic acrylamide polymerization. The water bath itself rests on a pneumatically operated vibration dampening platform which is activated and leveled by means of three valves. This permits the introduction of compressed nitrogen gas into three separate pneumatic cushions situated in a triangular arrangement beneath the vibration dampening platform. The pneumatic cushions rest upon a solid stone slab table to further protect the system from extraneous vibrations. Such vibrations could disturb the delicately positioned acrylamide gradient before or during polymerization.

Since four tubing channels are provided on each peristaltic pump, up to four individual casting chambers may be connected for gel casting with each run. A separate mixing chamber must be provided for each casting chamber. Since each casting chamber supports 8 gel cassettes, 32 gradient gels may be cast simultaneously. When four mixing chambers such as those shown in FIG. 1 are used during a run, the self purging capability is necessary since tipping four chamber simultaneously to remove air bubbles is not feasible.

In a preferred embodiment of the invention, a wider gel is cast in order to accommodate more samples for clinical applications. The size of the gel is limited by the possibility of premature polymerization during casting. Practitioners of the art can vary the speed of the pump to prevent premature polymerization of larger volumes.

Polymerization of the acrylamide is allowed to proceed. In a preferred embodiment, polymerization occurs in a minimum of 1 hour. In a more preferred embodiment, polymerization occurs for at least 12 hours.

Several gels can be prepared at one time, using an apparatus such as the GSC-8 Gel Slab Casting Apparatus (Pharmacia, Piscataway, N.J.).

Such gels can be prepared several weeks in advance, washed in distilled water, and stored at 4° C. in plastic bags with electrophoresis buffer and sodium azide as preservative. This would aid in the processing of large numbers of samples within a batch for clinical applications, and allows excellent homogeneity of product as the production environment is nearly identical for the simultaneously produced gels.

Test Samples

Venous blood samples are obtained from patients (who have abstained for 12–16 hours from all food), immediately transferred into tubes containing sodium EDTA (1 mg/l), and stored at 4° C. Optimally, samples should be analyzed within four days, but can be frozen at −80° C. until use. The samples are prepared by adding sucrose to a final concentration of 8%, and bromophenol blue to 0.05%. Only 3 $\mu$l of the plasma sample mixture is needed for loading on the gel.

Gel Markers

Commercially available molecular weight calibration markers that can be used include a mix of four high molecular weight globular proteins (HMW Calibration kit, Pharmacia) which contains thyroglobulin (170Å) and apoferritin (122Å). In addition, carboxylated latex beads of 380 Å (Duke Scientific Corp., Palo Alto, Calif.) can be added to the lane containing the high molecular weight markers, but must be loaded at least two hours after the gels have been run at 125V, or up to 10 hours before the end of the run.

Figure 8:
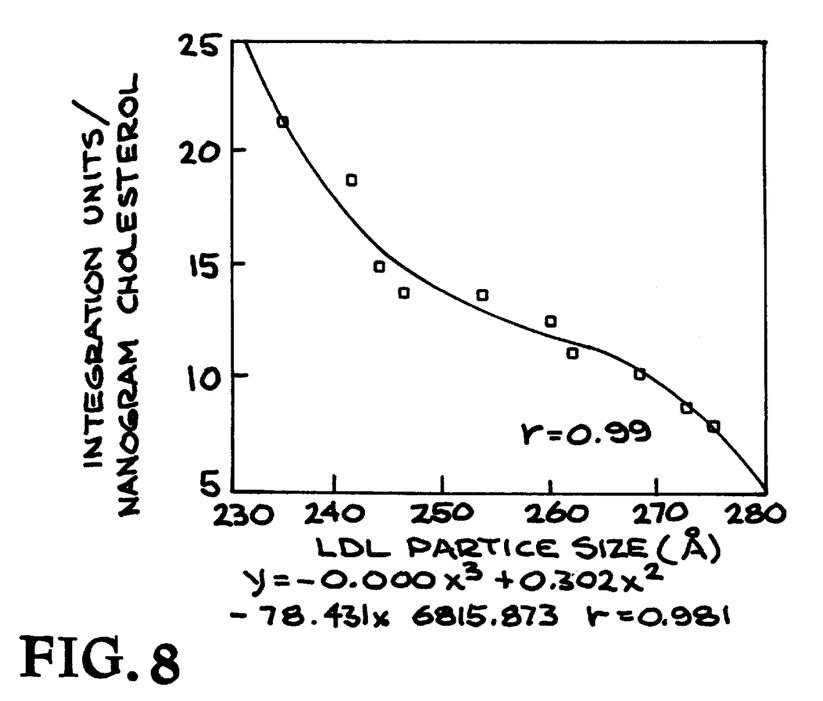
FIG. 8 is a graph showing cholesterol measured in the LDL subfractions and the variable area integration response according to particle size.

In one embodiment of the invention, previously sized and frozen low density lipoproteins are used as calibration markers. Any standards in the size range 120 Å to 380 Å that have been calibrated for particle size (for example, by electron microscopy) can also be used, as shown in FIG. 8. All samples and standards are mixed with a tracking dye, such as bromophenol blue, prior to loading. One typical algorithm for this determination is:

$$y=-0.000x^3+0.302x^2-78.43\times 6815.873 \; r=0.981.$$

II. Separation of LDL Subfractions

The gradient gel undergoes electrophoresis by conventional means to allow optimal separation of LDL subspecies, at which time the gradient gel is removed from the electrophoresis apparatus, fixed, and stained with a conventional lipid or protein staining dye. The LDL banding pattern of the gradient gel is detected by conventional methods by scanning with a densitometer. The information thus obtained is relayed to a computer.

Equipment

Basic equipment for conventional gradient gel electrophoresis includes a slab gel electrophoresis chamber, a constant voltage power supply, and a refrigerated circulating water bath.

The electrophoresis module, represented in FIG. 2, consists of the gradient gel plates assembled in an electrophoresis apparatus, such as Pharmacia GE-4 Gel Electrophoresis Apparatus. The upper end of the gel is attached to an upper chamber filled with running buffer, circulated from the lower chamber. The plasma samples and calibration markers are loaded in wells of a plastic sample holder inserted in the upper end of the gel.

Buffers

The preferred running buffer is tris-borate buffer (0.09M Tris, 0.003M $Na_2$ EDTA, 0.08M boric acid; pH 8.3), although other running buffers with pH 8.3 may be used. Among the buffers that can be modified to use in this system is a tris-glycine buffer.

Pre-electrophoresis (Gel Only)

The electrophoresis chamber is connected to a power supply and a constant voltage of 125V applied for 30 to 60 minutes.

Running Conditions (Gel with Loaded Samples)

After samples are loaded on the gel, the electrophoresis chamber is connected to a power supply and constant voltage applied, first at 40V for 15 minutes, then at 80V for 15 minutes, and finally at 125V for 24 hours (3000 volt hours). Any power supply that provides constant voltage up to 125V with variable amperage greater than 250 ma can be used; examples of models that can be used are Bio-Rad Model 500, LKB Model 2002, and Pharmacia Model EPS 400/500.

For best results, the gradient gel electrophoresis is run at 125V for 24 hours. A range of 22 to 26 hours is acceptable. A voltage range of 125V to 200V can be used, but the most preferred voltage is 125V. The buffer chamber is maintained at an optimal temperature of 10° C. by connecting the chamber to a circulating refrigerated water bath. This cooling process could also be achieved by performing the electrophoresis in a cold box. A preferred temperature range is 8° C. to 11° C. The most preferred temperature range is 9° to 10° C.

In a preferred embodiment of the invention, the polyacrylamide is strengthened by agarose. In a more preferred embodiment of the invention, a 1%–9% or 2%–9% gradient gel is used and the electrophoresis time is reduced to eight hours or less, facilitating the processing of multiple samples for clinical analysis.

In a preferred embodiment of the invention, multiple gels are run simultaneously in the electrophoresis chamber. This modification serves to speed processing of samples and reduces costs of processing clinical samples.

III. Identification of LDL Subfractions

Staining

The staining module consists of a plastic tray in which the gradient gel (after removal from glass plates) is fixed, stained and washed. In one embodiment, the gel is fixed and stained for lipid in 60% ethanol containing Sudan Black B (Beckman, Kit P/N 655910) in a 55° C. oven for at least 18 hours but no more than 22 hours, and destained. The lane containing high molecular weight protein standards is then covered with a paper filter strip and stained for protein for at least 30 but no more than 60 minutes with Coomassie R-250 Blue stain (Bio-Rad).

Other lipid stains that can be used include Oil Red O (scanned at 530 nm). The choice of stain used is constrained by the light source of the densitometer used to scan the gel. Stains specific for other chemical groups within lipoprotein structures can also be used (including periodic acid-Schiff reagent for interaction with carbohydrate groups in apolipoprotein). Optimal staining time is dependent on the type of stain used. In a preferred embodiment of the invention, the gel is stained in a pressure-temperature controlled container mounted on a magnetic stir motor for a shorter and specific period of time (4 to 6 hours) for rapid processing of clinical samples. In this novel staining device, gels are suspended vertically and separated from one another in a dye chamber equipped with a framework for hanging polyethylene mesh gel holders designed to support each gel. Dye is continuously circulated in the container by use of a magnetic stir bar. Gel holders are prepared from strips of mesh with pore size less than 150 $\mu$m which are folded, heat-sealed in the lower portion of two sides and left open on top to insert the gel. A plastic rod serves to hang the holder from the top of the dye chamber.

Scanning

The scanning module, as shown in FIG. 2, consists of a densitometer which is used to scan individual lanes of the gradient gel for the lipid-stained LDL banding pattern (530 nm), and computer software which stores this information in a computer. Optical density is measured by computer-assisted densitometry at 0.01 nm (0.1 Å) intervals across the LDL diameter range (220–285 Å) in lipid-stained gels. In one embodiment, a densitometer with good quality optics and a laser light source, such as Molecular Dynamics Model #PD, is used in conjunction with a VAX station 3200 (DEC, Maynard, Mass.). The densitometer must be capable of a highly controlled rate of transport (for scanning) the gel. In addition, the densitometer must scan the gel at 0.1 Å intervals in less than one hour. Optimally, one gel can be scanned within seven minutes.

In an alternative embodiment, a negative of a photo of the gel is scanned. This procedure improves stability of information, while possibly reducing resolution of LDL separation.

IV. Data Analysis

Referring to FIG. 5, the analysis module (as shown in FIG. 2) is shown to consist of five analytical steps performed by software analysis of the densitometric scans of the gradient gel banding pattern. In the first analytical step, peak particle sizes for each of the absorbance maxima are calculated from migration distances, from a calibration curve using the calibration standards of known diameters. In the second analytical step, the area associated with LDL subclasses in the densitometer scan is obtained by integration of the scan within LDL subclass particle size intervals. The area of the densitometric scan between each particle size interval is then converted to a concentration of an LDL subclass in the third analytical step. In the fourth analytical step, a corresponding cholesterol concentration is assigned to each LDL subclass, based on accumulated patient data stored in the software program. In a final step, based on the levels of a specific LDL subspecies LDL-IIIa, IIIb, and IVa, and the cholesterol associated with them, the patient is assigned a risk factor for coronary artery disease.

Figure 6:
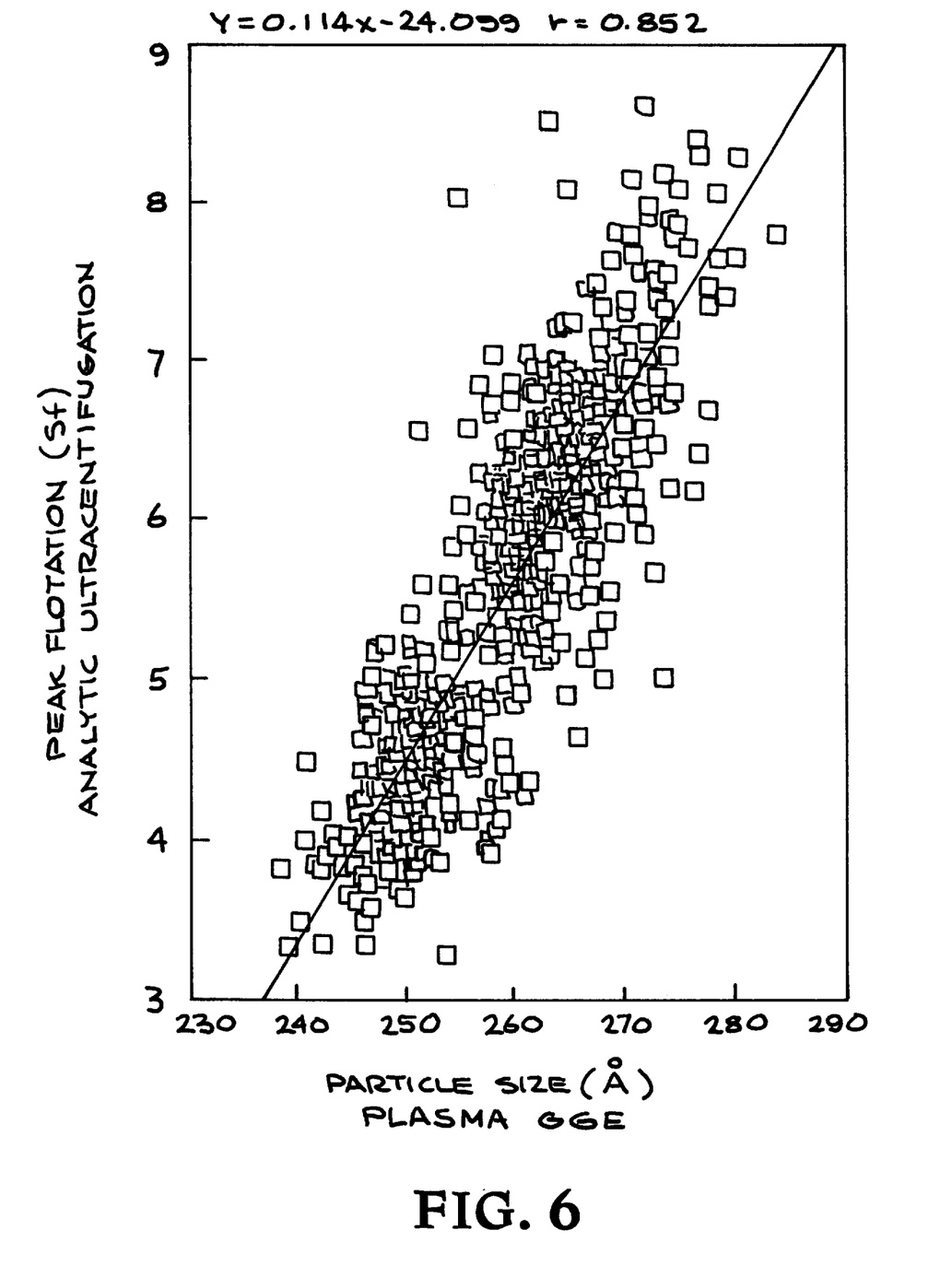
FIG. 6 is a graph comparing the peak particle size of LDL subspecies derived from gradient gel analysis of plasma.
Figure 7:
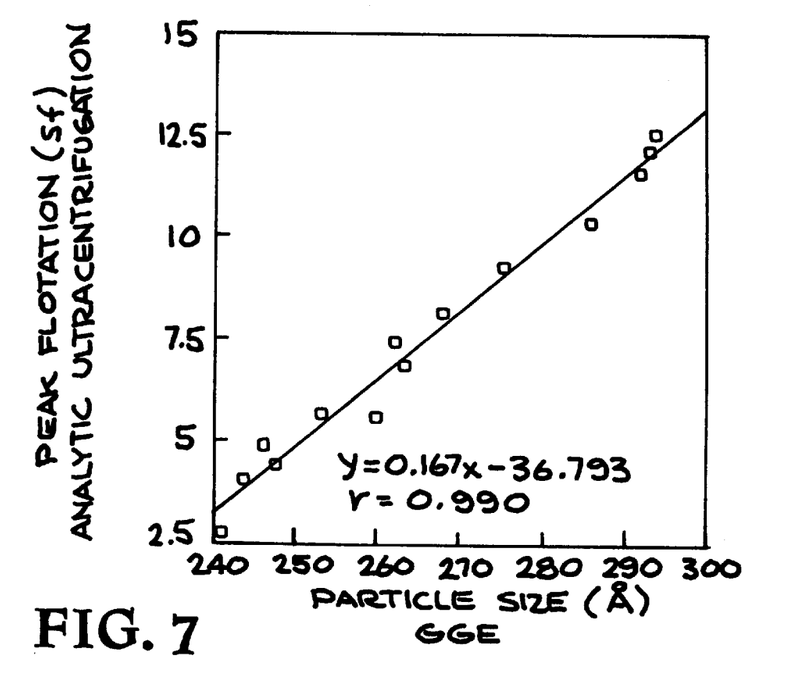
FIG. 7 is a graph comparing the peak particle size from gradient gel analysis of LDL subspecies derived from partially purified LDL samples with LDL subspecies resolved by analytic ultracentrifugation.

FIG. 6 is a graph comparing the peak particle size of LDL subspecies derived from gradient gel analysis of plasma as in Example 1, with LDL subspecies resolved by analytic centrifugation. FIG. 7 is a graph comparing the peak particle size from gradient gel analysis of LDL subspecies derived from partially purified LDL samples as in Example 2, with LDL subspecies resolved by analytic ultracentrifugation.

SELF-PURGING MIXING CHAMBER

As shown in FIG. 1, the inventive mixing chamber is composed of several components which, when fitted together by means of interlocking threaded surfaces, produce a single unit. One particularly advantageous feature of the inventive mixing chamber is the provision for entry of starting materials at the bottom of the chamber and exit at the top of the chamber for purging air bubbles when the acrylamide solution first enters the chamber.

The provision for bottom entry of starting materials of the inventive chamber minimizes or eliminates the production and integration of bubbles into the production tubing and into final gel product.

By positioning the entry port at the top corner of the mixing chamber at 45° to its horizontal surface, the distance between the magnetic stir star and the magnetic impeller of the motorized stir plate, upon which the inventive mixing chamber rests, can be minimized. This feature permits the greatest possible torque to be developed by the stir star in the mixing chamber and the greatest possible angular velocity of the stir star to be obtained. The maximum mixing capability and minimum chance that the stir star may stop turning during the gel casting operation is afforded by this arrangement. In fact, in a previous prototype mixer in which the stir-star was positioned 1 cm above the stir plate the stir star would stop performing as the acrylamide solutions were pumped by it.

The preferred stir plate is a multiple position electronic stirrer from Fisher Scientific. Since no motors turn to drive the stir star, vibrations are reduced and a more stable environment is provided for the final gradient. The static volume of the assembled mixing chamber is 1 mL and the digitally set velocity of the stirrer is 1100 RPM. Since the constant velocity of solutions through the mixing chamber is 7 mL/min, each 1 mL of acrylamide solution is mixed by 157 revolutions of the stir-star.

Situating the entrance at an acute angle to the chamber's vertical axis, rather than entering at a right angle from the side, permits the magnetic stir star to be in close proximity to the magnetic impeller placed under it. This allows a more direct drive.

The inventive chamber is particularly suited to continuous production, and parallel production, of gels. The inventive approach is well suited to the production of gels with highly controlled progressive densities described in the present application. Self purging chambers permits multiple channels to be pumped simultaneously without manipulation. Prior art mixing chambers provided for the starting materials to enter on one side and exit from the other, causing a bubble to be trapped in the chamber, or requiring manual repositioning of the chamber to clear the bubble.

The use of threaded surfaces to provide for assemblage has several advantages. This means of assemblage provides for the water tight seals necessary for the correct passage of the various liquid components and products of the final gel product through the assemblage. It also allows easy disassemblage of the unit for cleaning, repairs, and to modify certain parameters of filling and mixing.

The assemblage is preferably constructed of a lucite or other transparent polymeric material. This allows continuous observation of the mixing process, avoiding loss of time and product if difficulties such as non-turning magnet, occluded passages, leaking seals or other problems arise during a mixing run. Modifications of protocol are also more practical, as the actual flow and processing of materials can be observed during the cycling period.

The inventive assemblages have the advantage of being relatively small, and highly reliable. A relatively mild warming bath is all that is necessary to maintain the necessary temperature parameters for the gel processing protocol. Both the small size and reliability of the system allows for multiple, parallel processing of components for several gels at the same time in a single water bath. While providing a substantial savings in time and money when multiple gels are desired, this parallel production also produces gels of remarkable consistency, as all parameters for production are identical.

Upper plug 1 is shown in FIG. 1 as a cutaway view, and is cylindrical in shape. It is a solid delrin monolith from which various features are developed by boring, tapping and other means of working. Delrin is an easily machined plastic substance with sufficient strength to be tightened into the main body to press the plug against the Teflon gasket, forming a water tight seal. A plug of lucite would splinter, crack or chip under such force.

The top surface portion of the upper plug 1 is circular in shape, and 0.750" in diameter with a circular bore at its center. Upper plug 1 also has a shoulder section 3, which is 0.1875" in height. The total upper plug 1 height top to bottom is 0.6425".

The upper plug 1 is additionally provided with an upper bore 5 which is generally cylindrical in shape, and measures 0.365 inches top to bottom along its central axis. Upper bore 5 is provided on its vertical surfaces with inside threads 7 which are $3/8 \times 24$ NPT. Upper bore 5 is also provided with a shallow funnel portion 9 at its lower end.

Descending from the lower point of the shallow funnel portion 9 is a cylindrical narrow channel (0.0625 diameter) 11 which connects to a shallow conical bore 13 provided at the inner cylindrical dimension of the lower surface of upper plug 1. Thus, a continuous pass-through channel is provided through upper plug 1 from bottom to top with its core centered on the central axis of upper plug 1.

The outside of the upper plug 1 is larger at the top, as provided by shoulder section 3, and then tapers to a cylindrical lower portion 15, which is 0.455" in height from the lower point of shoulder section 3 to the bottom of the upper plug 1. The taper is not critical so long as the bottom surface of the plug 1 seats against the teflon gasket 19 before the shoulder 3 contacts the top surface of the main body 1. The external surface of the lower portion 15 is provided on its surface with lower portion threading 17, which is $9/16 \times 18$ NPT.

Teflon gasket 19 is used to seat upper plug 1 over teflon-coated stir-star 21 in main body 23. The teflon gasket 19 has an outside diameter of 0.52" and an inside diameter of 0.41"×0.007". Stir-star 21 has a vertical dimension of 0.318" and a horizontal dimension of 0.366".

Main body 23 is a solid lucite cylindrical monolith into which a number of chambers have been bored. The preformed cylinder which is worked into the final main body 23 has the dimensions of 0.850" in height by 2.008" in diameter. One short side upper edge of the box is milled diagonally.

A cylindrical box 25 has a diameter of 0.28" and is provided extending down from the top surface of the main body 23. It has threading 27 on its vertical cylindrical surface, and is 0.460" in height.

In the processing of gel mixtures, the box 25 is mated to the cylindrical lower portion 15 of upper plug 1 by way of lower portion threading 17 being screwed into the box threading 27. The lower surface of box 25 is provided with a shoulder 29 whose inner diameter is 0.208". Teflon gasket 19 seats on shoulder 29 prior to the insertion of upper plug 1 in order to assure complete sealing of the unit.

Lower chamber 31 is provided in main body 23 beneath box 25 on a common central axis. The lower chamber 31 has a smaller diameter than the box 25, which is 0.208", and allows good structural integrity of the final assemblage, as well as ease of cleaning. The lower chamber 31 is 0.335" in height and 0.054" above the lower surface, and should be no more than 0.10". This allows the necessary proximity of the magnetic stirrer for proper torque. Teflon coated stir-star 21 is maintained in the lower chamber 31 by means of this configuration.

Main body 23 is further provided with diagonal chamber 33, whose central axis runs from the diagonally milled upper edge downwards towards the bottom of the main body 23. The diagonal chamber 33 has a length of 0.365", and is provided with threading 35 on its internal cylindrical surface. At the base of diagonal chamber 33 is a funnel base 37.

Connecting the diagonal chamber 33 to the lower chamber 31 is the diagonal narrow channel 39, which is 0.125" in diameter and exits from the funnel base 37 and has a cylindrical axis in common with diagonal chamber 33. This axis is at a 45° angle from the bottom surface of the main body 23. These features provide a continuous channel from the upper plug 1 through the main body 23.

The inlet body 39 is generally cylindrical and has an inlet barb 41 which allows the attachment of tubing directly to the completed assemblage. The inlet body 39 is provided with an inner bore 42 along its central axis, which opens to a larger bore 49 leading to a terminal exit through a funnel shaped bore 47.

The lower portion 43 of the inlet body 39 is externally provided with threading 45. The threading 45 mates with the threading 35 of the diagonal chamber 33, to provide a full integration of the inlet body 39 and the main body 23 through the diagonal chamber 33 once the components are assembled.

Variable diameter nylon gasket 51 is designed to provide a water-tight seal between the inlet body 39 and the diagonal chamber 33 of the main body 23. The nylon gasket 51 can be exchanged for other nylon gaskets with different internal diameters to vary the rate of flow of materials into the assembled mixer.

The variable diameter nylon gasket 51 has a central port 53 which is on the central axis of nylon gasket 51. Positioning of the nylon gasket 51, is determined by the diagonal chamber 33 of the main body 23, and by the matching taper 47 of 39.

The half spherical lower surface 57 of nylon gasket 51 is shaped to fit funnel base 37 of main body 23. The conical upper surface 59 of nylon gasket 51 is shaped to fit funnel shaped bore 47 of the inlet body 39. These features allow the nylon gasket 51 to be snugly positioned between the inlet body 39 and the diagonal chamber 33 of the main body 23, providing an air and water tight seal.

EXAMPLE 1

A 2%–14% gel was prepared from stock solutions 1) 134.4 g/l acrylamide (Bio-Rad Laboratories, Richmond, Calif.), 5.6 g/l bis-acrylamide (Bio-Rad), and 50 g/l sucrose in tris-borate buffer (pH 8.3) (14.0% total, 4.17% cross-linker), and 2) 15.6 g/l acrylamide, 0.92 g/l bisacrylamide in tris-borate buffer (pH 8.3) (2% total, 5.9% crosslinker). The stock solutions were vacuum-filtered and stored at 4° C. for less than one month, prior to gel casting. The high limit solution was made immediately prior to casting the gradient, and contained for each set of 8 gels 85 ml solution 1, 85 $\mu$l of freshly prepared 10% ammonium persulfate (Sigma Chemical Company, St. Louis, Mo.), and 42.5 ml of 3-dimethylaminopropionitrile (Sigma). The low limit solution was also made immediately prior to casting the gradient, and contained for each set of 8 gels 85 ml solution 2, 850 $\mu$l 10% ammonium persulfate, and 18.2 $\mu$l 3-dimethylaminopropionitrile. The approximate dimensions of this gel were 8 cm width by 7.2 cm length.

A dual Wiz-pump gradient controller (ISCO, Lincoln, Neb.) was used to cast the gradients. This system is preferred because the solutions are retained in disposable plastic tubing, the pumps are easily calibrated for each occasion using the software, and the gradients are reproducibly generated by the computer. In this system, two pumps were separately controlled by an Apple IIe computer (Apple Computer, Inc., Cupertino, Calif.) via a ChemInterface unit and software (ISCO). 80 ml of the low limit solution and 80 ml of the high limit solution were mixed in an custom-designed external mixing chamber (mixing volume of 0.76 ml, with a 2.8×10 mm stirbar) before entering the casting stand. The gradient was pumped at a rate of 7.0 ml/minute from the bottom under a 20 ml layer of ethanol-water 1:4 (v/v). Afterward, 18 ml of a 60% sucrose solution was pumped into the chamber to displace the gradient upward.

The gel was allowed to polymerize for 2 hours. Electrophoresis was carried out at 12–14° C., using Tris (0.09M)-boric acid (0.08M)Na$_2$EDTA (0.003M) buffer, pH 8.3. Gels were prerun at 125V for 15 minutes prior to loading samples.

Plasma samples or standards were mixed 4:1 with tracking dye (40% sucrose; 0.25% bromophenol blue); 3 $\mu$l of plasma or 6 $\mu$l of standard was applied to each lane of the gradient gel. The standards comprised a mixture of four globular proteins (HMW Calibration Kit, Pharmacia, Piscataway, N.J.) including thryroglobulin and apoferritin. Latex beads were added to the high molecular weight standard lane (after two hours of electrophoresis) to determine particle diameter. Voltage was first adjusted to 40V for 15 minutes, then 80V for 15 minutes, and finally 125V for 24 hours. For lipid staining, the gel was fixed with 50% methanol plus 10% acetic acid and stained overnight in a 55° C. oven with 0.04% Oil Red 0 (Sigma) in 60% ethanol, and scanned at 530 nm with a Transidyne RFT densitometer (Transidyne Corporation, Ann Arbor, Mich.).

Scan data were processed on a VAX Station 3200 (DEC, Maynard, Mass.). Migration distances ($R_f$) for each of the absorbance maxima were measured from the beginning of the gel. Peak particle sizes were calculated from a calibration curve using the standards of known diameters: calculus (transformation of variables) was used to transform the LDL distribution from the migration distance scale to the particle diameter scale. In addition, a second plasma aliquot was separated into constituent LDL subspecies by analytic ultracentrifugation for comparison. Table 5 depicts the graph comparing the separation of plasma LDL subspecies by the two techniques, showing that the two techniques yield the same banding pattern. We correlated flotation properties of LDL with lipid-stained LDL absorbance for all diameter values between 21.8 and 32 nm, for the individual flotation intervals $S_f 0-1$, $S_f 1-2$, . . . $S_f 12-14$. A quadratic regression curve fitted through the points provides an estimate of the correspondence between flotation rate and diameter. The curve between $S_f 1.5$ and 13 has the formula:

diameter=23.78+0.18×flotation rate+0.03×flotation rate

Table 5 is the graph comparing LDL subspecies separation obtained by the present invention with those obtained by analytic ultracentrifugation, showing good correlation between the two methods.

EXAMPLE 2

In this example, isolated LDL subfractions from ultracentrifugation were analyzed further by gradient gel electrophoresis. A gradient gel was formed with a 2–14% polyacrylamide gradient, using a Wiz dual-pump gradient controller (ISCO, Lincoln, Neb.) run by a ChemInterface unit and ISCO software to control the flow rate at 7.0 ml/minute. 80 ml of the low limit solution and 80 ml of the high limit solution were mixed in an external mixing chamber before being pumped into the casting stand from the bottom under a 10 ml layer of ethanol-water (1:4)(v/v), for an approximate preparation time of 20 minutes. At this time, 18 ml of sucrose solution (600 g/L) was pumped into the chamber to displace the gradient upward to the bottom of the glass plates. The gel was allowed to polymerize for 2 hours. Electrophoresis was carried out at 10° C., using Tris (0.09M)-boric acid (0.08M)-$Na_2$EDTA (0.003M) buffer, pH 8.3. Gels were prerun at 125V for 15 minutes prior to loading samples.

Plasma fractions were mixed 4:1 with tracking dye (40% sucrose; 0.25% bromophenol blue); 3 $\mu$l of plasma or 6 $\mu$l of standards (Pharmacia HMW; and Lpcal-C VL lipoprotein calibrator) was applied to each lane of the gradient gel. Latex beads were added to the high molecular weight standard lane after two hours of electrophoresis. Voltage was gradually increased from 40V for 15 minutes, then 80V for 15 minutes, and then 125V for 24 hours.

For lipid staining, the gel was fixed with 50% methanol plus 10% acetic acid and stained overnight in a 55° C. oven with 0.04% Oil Red O (Sigma) in 60% ethanol, and scanned at 530 nm with a Transidyne RFT densitometer (Transidyne Corporation, Ann Arbor, Mich.).

Scan data were processed on a VAX Station 3200 (DEC, Maynard, Mass.). A second plasma aliquot was separated into constituent LDL subspecies by analytic ultracentrifugation for comparison. FIG. 6 depicts the graph comparing the separation of the plasma LDL subspecies by the two techniques, showing that the two techniques yield the same banding pattern.

FIG. 7 is the graph comparing LDL subspecies separation obtained (after partial purification) by the present invention with those obtained by analytic ultracentrifugation, showing good correlation between the two methods.

EXAMPLE 3

As in Example 2, isolated LDL subfractions from equilibrium density ultracentrifugation were further analyzed by gradient gel electrophoresis. Subfractions were additionally analyzed for chemical composition including cholesterol and triglyceride by enzymatic endpoint assay, phospholipid, and apolipoprotein B. FIG. 8 is the graph showing cholesterol measured in the LDL subfractions and the variable area integration response according to particle size. This data represents integration units per nanogram of cholesterol applied to the gel throughout the LDL particle size range.

EXAMPLE 4

A gradient gel is formed with a 2–9% polyacrylamide gradient, using the Wiz dual-pump gradient controller and ISCO software. 70 ml of the low limit solution and 32 ml of the high limit solution are mixed in an external mixing chamber before being pumped into the casting stand from the bottom under a 10 ml layer of water-ethanol (1:4), for an approximate preparation time of 14 minutes. Then, 18 ml of sucrose solution (60%) is pumped into the chamber to displace the gradient upward. The gel is allowed to polymerize for 2 hours, then prerun at 125V for 15 minutes at 10° C. in tris-borate buffer.

Three microliters each of plasma sample mixture or calibration markers (frozen lipoproteins that have been sized by electron microscopy) are loaded on individual lanes of the gel. Voltage is gradually increased from 40V for 15 minutes, then 80V for 15 minutes, and then 125V for 8 hours at 10° C. The gel is removed from the cassette, stained in Sudan Black, washed, and stained again for marker proteins with Coomassie R250 Blue.

After densitometry scanning and data analysis, the lipoproteins are seen to be identical to those identified with the 2–14% gel. Thus, the time for the gel electrophoresis procedure for separating the lipoprotein bands can be shortened by one-third without any loss of resolution or accuracy.

EXAMPLE 5

A step gradient gel is prepared with a 1%–9% polyacrylamide gel, with 2% agarose added to the gel mixture. The agarose strengthens the gel so that electrophoresis can occur at room temperature (rather than at 10° C.), simplifying the procedure. The 1% low limit of the gradient gel allows separation of larger lipoproteins. The gel is run for 2750V.h in tris-borate buffer, and is stained, washed and scanned at 530 nm using the Molecular Dynamics Model PD and VAX system. The analysis now includes data for lipoproteins in the size range 400–500 Å, as well as the 220–285 Å range.

Thus, the invention provides an apparatus to achieve rapid and inexpensive quantitation of LDL cholesterol subclasses in an rapid, accurate and direct manner, enabling it to be used in a clinical laboratory, and with greater resolution than that achieved by the prior art. In addition, it provides the direct assignment of a patient risk factor for coronary artery disease.

The description of illustrative embodiments and best modes of the present invention is not intended to limit the scope of the invention. Various modifications, alternative constructions and equivalents may be employed without departing from the true spirit and scope of the appended claims.

We claim:

1. A segmented electrophoretic gradient gel for the separation and quantitation of lipoprotein subfractions, said lipoproteins being electrophoresed along a length of the gel consisting essentially of a polymer gel structure having an overall polymer percentage ranging from about 0.5% to 2% to a maximum of about 9% to 20% with three adjacent segments, each with a different rate or increasing polymer percentage;
a) said first segment having the highest rate of increasing polymer percentage of the three segments,
b) said second segment having the lowest rate of increasing polymer percentage of the three segments, and
c) said third segment having an intermediate rate of increasing polymer percentage which is between the rates of increasing polymer percentage of said first and second segments.

2. The gel of claim 1, wherein total gel varies in polymer percentage from top to bottom from about 0.5%–20%.

3. The gel of claim 2, wherein the total gel varies in polymer percentage from top to bottom from about 1%–16%.

4. The gel of claim 3, wherein the total gel varies in polymer percentage from top to bottom from about 1%–14%.

5. The gel of claim 4, wherein the total gel varies in polymer percentage from top to bottom from about 2%–14%.

6. The gel of claim 1, wherein the first segment comprises from 5%–15% of the gel length, and varies in polymer percentage from surface to surface from 2% to between 3%–5%.

7. The gel of claim 6, wherein said first segment varies in polymer percentage from surface to surface from about 2% to 3.7%.

8. The gel of claim 1, wherein said second segment comprises from 50%–70% of the gel length, and varies in polymer percentage from surface to surface from between 3%–5% to between 8%–12%.

9. The gel of claim 8, wherein said second segment varies in polymer percentage from surface to surface from about 3.7% to about 9.7%.

10. The gel of claim 1, wherein said third segment comprises from 15%–45% of the gel length, and varies in polymer percentage from surface to surface from 8%–12% to between 12%–16%.

11. The gel of claim 10, wherein said third segment varies in polymer percentage from surface to surface from about 9.7% to about 14%.

12. The gel of claim 1, wherein the polymer gel is selected from acrylamide, agarose, and N-acryloyl-tri (hydroxymethyl) aminomethane.

* * * * *